United States Patent [19]

Miyadera et al.

[11] Patent Number: 5,798,213
[45] Date of Patent: Aug. 25, 1998

[54] MONOCLONAL ANTIBODIES

[75] Inventors: Kazutaka Miyadera, Kagoshima; Yuji Yamada, Saitama; Yuji Takebayashi; Shinichi Akiyama, both of Kagoshima, all of Japan

[73] Assignee: Taiho Pharmaceutical Co., Ltd., Tokyo, Japan

[21] Appl. No.: 696,827

[22] PCT Filed: Dec. 25, 1995

[86] PCT No.: PCT/JP95/02661

§ 371 Date: Aug. 21, 1996

§ 102(e) Date: Aug. 21, 1996

[87] PCT Pub. No.: WO96/20217

PCT Pub. Date: Jul. 4, 1996

[30] Foreign Application Priority Data

Dec. 28, 1994 [JP] Japan ................... 6-327328

[51] Int. Cl.⁶ .............. G01N 33/573; G01N 33/536; G01N 33/577; C07K 16/24
[52] U.S. Cl. .............. 435/7.4; 435/7.1; 435/960; 435/331; 435/335; 435/336; 435/337; 435/338; 435/332; 530/388.2; 530/388.23; 530/388.26; 530/389.2; 530/391.1; 935/104; 935/108
[58] Field of Search ................. 435/7.1, 7.4, 240.27, 435/960, 331, 335, 336, 337, 338, 332; 436/501, 536; 530/388.2, 388.23, 388.26, 389.2, 391.1; 935/104, 108

[56] References Cited

U.S. PATENT DOCUMENTS 5,227,302 7/1993 Heldin et al. .................. 435/357

FOREIGN PATENT DOCUMENTS 2-288897 11/1990 Japan.

OTHER PUBLICATIONS

Sumizawa, T. et al. "Thymidine Phosphorylase Acitvity Associated with Platelet–Derived Endothelial Cell Growth Factor", J. Biochem. (1993) vol. 114, No. 1, pp. 9–14.

Osamu Kanemitsu "Introduction of Antibody", Jan. 25, 1994 (25.01.94), Chijinshokan pp. 75–144.

Furukawa et al., Nature, 356:668, 1992.

Ishikawa, F. et al. "Identifiecation of Angiogenic Activity and the Cloning and Expression of Platelet–Derived Endothelial Cell Growth Factor", Nature (1989) vol. 338, pp. 557–562.

Takeuchi et al., Arth. and Rheumat., 37:662–672, 1994.

Primary Examiner—Ronald B. Schwadron
Attorney, Agent, or Firm—Sughrue, Mion, Zinn, Macpeak & Seas, PLLC

[57] ABSTRACT

The present invention provides monoclonal antibodies against peptides having an amino acid sequence described in Sequence No. 1 or No. 2, the peptides being found in human thymidine phosphorylase and human platelet-derived endothelial cell growth factor. The Invention also provides an immunoassay for human thymidine phosphorylase and/or human platelet-derived endothelial cell growth factor using the monoclonal antibodies. The monoclonal antibodies of the invention recognize human thymidine phosphorylase and human platelet-derived endothelial cell growth factor, and thus are useful in the diagnosis and treatment of various tumors and their metastasis and diseases accompanying abnormal angiogenesis.

6 Claims, 3 Drawing Sheets

2A4

2D9

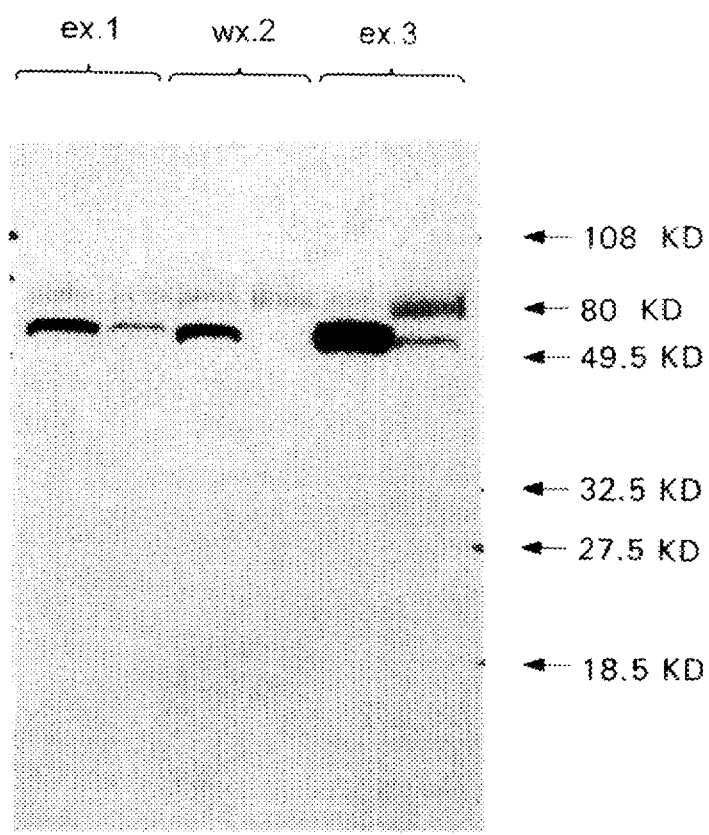

MONOCLONAL ANTIBODIES

This application is a 371 of PCT/JP95/02661 filed Dec. 25, 1995.

TECHNICAL FIELD

The present invention relates to monoclonal antibodies which are useful for the detection of human thymidine phosphorylase and the platelet-derived endothelial cell growth factor (PD-ECGF), i.e., for the monitoring via diagnosis and treatment of a variety of tumors, diseases involving abnormal angiogenesis such as metastasis of tumors, rheumatic arthritis, diabetic retinitis, immature cataract, senile macular degeneration, etc., as well as for use in drug delivery systems for medicine, etc.

TECHNICAL BACKGROUND

Thymidine phosphorylase is an enzyme essential to the metabolism of thymidine and has been reported to manifest its activities in different tissues (liver, lungs, small intestine, large intestine, placenta, etc.) of humans and animals [J. Natl. Cancer Inst., 58, 1587–1590 (1977)]. Thymidine phosphorylase has also been reported to exhibit higher levels of activity in various malignant tumors than in normal tissue [Chem. Pharm. Bull., 34, 4225–4232 (1986)]. Because of this feature, thymidine phosphorylase is a target enzyme for an anticancer agent.

It is also reported that activity of PD-ECGF becomes elevated when abnormal angiogenesis occurs as compared to normal tissue [Nature, 338, 557–562 (1989)], which makes PD-ECGF a marker of diseases accompanying abnormal angiogenesis.

Recently, human thymidine phosphorylase has been reported to be genetically identical to PD-ECGF [Nature, 338, 557–562 (1989), Nature, 356, 668 (1992), and J. biochem., 114, 9–14 (1993)]. Measurement of thymidine phosphorylase activity and PD-ECGF activity is useful in the diagnosis of not only malignant tumors but also diseases involving abnormal angiogenesis, such as rheumatic arthritis, diabetic retinitis, immature cataract, senile macular degeneration, etc.

Conventionally, activities of human thymidine phosphorylase and PD-ECGF have been determined by measuring them in tissue. Therefore, excision of necessary amounts of tissue and fractionation of a crude enzymatic fluid must be performed, calling for cumbersome handling techniques. In addition, detailed comparison on the intercellular level cannot be made by conventional methods, raising a great problem in both the practical and accuracy aspects.

DISCLOSURE OF THE INVENTION

Accordingly, an object of the present invention is to provide simple, widely-applicable, and practical means which enables specific measurement of thymidine phosphorylase/PD-ECGF.

The present inventors conducted careful studies, created monoclonal antibodies using as immunogens certain peptides in human thymidine phosphorylase and PD-ECGF protein, and found that they specifically recognize human thymidine phosphorylase and PD-ECGF and thus are useful for the diagnosis of various diseases accompanying elevated human thymidine phosphorylase activity and PD-ECGF activity. The present invention was accomplished based on this finding.

Accordingly, the present invention provides a monoclonal antibody against a peptide having an amino acid sequence described in Sequence No. 1, a peptide having an amino acid sequence described in Sequence No. 2, or against a peptide recognized by the presence of either one of these two peptides which serves as an antigen site.

The present invention also provides an immunoassay for human thymidine phosphorylase and/or PD-ECGF using the above monoclonal antibody.

BRIEF DESCRIPTION OF THE DRAWINGS

FIG. 2 is a chart showing results of comparison in expression between human breast cancerous tissue which reacts with a monoclonal antibody of the present invention and its adjacent normal tissue (3 cases).

BEST MODE FOR CARRYING OUT THE INVENTION

Figure 1A:
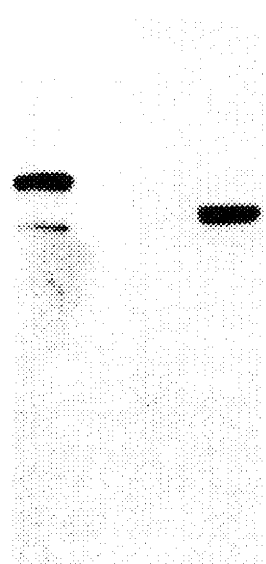
FIGS. 1A–1B are a chart showing profiles of reaction specificity of monoclonal antibodies of the present invention.

The peptide having an amino acid sequence described in Sequence No. 1 constitutes a portion of human thymidine phosphorylase, as does the peptide having an amino acid sequence described in Sequence No. 2. The peptide recognized by the presence of either one of these two peptides which serves as an antigen site is not particularly limited so long as it contains an amino acid sequence described in Sequence No. 1 or 2. Examples of such a peptide include human thymidine phosphorylase, PD-ECGF, fragmentary peptides which are portions of human thymidine phosphorylase or PD-ECGF and which contain an amino acid sequence described in Sequence No. 1 or 2, and peptides obtained by binding any of these peptides to a carrier protein. Examples of the carrier protein include, but are not limited to, glutathione-s-transferase (GST), hemocyanine of Keyhole limpet hemocyanin (KLH), etc.

The monoclonal antibodies of the present invention may be prepared, for example, by the cultivation of clones which produce antibodies that recognize as antigens the aforementioned peptides.

Such clones are obtained using a conventional cell fusion method; i.e., forming fusion hybrids between antibody-producing cells and myeloma cells, cloning the hybrids, and selecting clones producing antibodies that recognize as antigens the aforementioned peptides.

Examples of the antibody-producing cells used herein include spleen cells, lymph node cells, and B lymphocytes, all of which are obtained from animals immunized using, as antigens, peptides having the amino acid sequence of Sequence No. 1 or 2, peptides recognized by the presence of either one of these two peptides serving as an antigen site, or binding products of any of these peptides and a carrier protein.

The antibody-producing cells are prepared by routine methods. For example, an antigen is first emulsified in a complete or incomplete Freund's adjuvant to obtain an antigen suspension. Immediately thereafter, the suspension is subcutaneously or intraperitoneally injected into an animal every 2–3 weeks for several times (preferably 3 times), thereby immunizing the animal. Examples of animals which are immunized include mice, rats, horses, goats, rabbits, etc. Three to five days after the final immunization performed via intravenous administration of antigen, antigen-producing cells such as spleen cells are harvested from the immunized animal.

As the myeloma cells, those derived from mice, rats, and humans are used. Preferably, myeloma cells derived from the same animal from which the antigen-producing cells are harvested are used. For example, as a fusion counterpart of murine spleen cells, murine myeloma cells such as P3UI and SP-2/O-Ag 14 [Nature, 277, 131–133 (1979)] may be used.

Fusion of cells is performed using a method described in Nature 256, 495–497 (1975), or the method described by Ueda et al. in Proc. Natl. Acad. Sci. U.S.A 78, 5122–5126 (1981) or its equivalent method. Generally, 30–50% polyethylene glycol (average molecular weight: 1000–4000) is used in a fusion reaction, and the reaction proceeds at 30°–40° C. for 1–3 minutes. More preferably, 30–50% polyethylene glycol (average molecular weight: 4000) is used in a fusion reaction, and the reaction proceeds at 37° C. for 1–3 minutes.

The hybridoma obtained by cell fusion are subjected to culturing in, for example, a microplate using an HAT medium (basal medium containing hypoxanthine 100 μM, aminopterin 0.4 μM, thymidine 16 μM) or a similar medium, after which the grown cells are selected. The selected hybridomas are subjected to an antigen-binding assay and then to cloning.

Briefly, antigen titer of the supernatant of the wells in which growth of cells was observed is determined by an enzyme antibody technique such as ELISA (enzyme-linked immunosorbent assay, Miller, M. E., Lancet, 1, 665 (1971)) using an antigen peptide as antigen for screening. Subsequently, cloning is performed using a limited dilution method, thereby obtaining clones.

When the thus-obtained clones are cultured like ordinary animal cells, the monoclonal antibodies of the present invention are produced in the medium. Since these clones, when intraperitoneally implanted in a Balb/c mouse to which 0.5 ml of pristan has been administered in advance, produce ascites containing high levels of monoclonal antibodies on day 7–14, the monoclonal antibodies of the present invention can also be collected from ascites.

The monoclonal antibodies of the present invention can be recovered from the culture mixture or ascites containing the clones by the application of a well-known method for the purification of IgG, including a variety of chromatography procedures using anion exchangers, hydroxyapatite, or protein A- or G-immobilized columns; ammonium sulfate fractionation method; PEG fractionation method; ethanol fractionation method; or a hypotonic buffer precipitation method.

Among the thus-produced monoclonal antibodies of the present invention, those belonging to the class IgG are preferred.

Among the monoclonal antibodies of the present invention, those obtained using the entirety of human thymidine phosphorylase as antigen are less preferred than those obtained using as antigen a peptide which is a portion of human thymidine phosphorylase and which contains an amino acid sequence of Sequence No. 1 or 2, or a binding product of such a peptide and a carrier.

The monoclonal antibodies obtained by the use of human thymidine phosphorylase fragments as antigen exhibit lower cross-reactivity to exogenous proteins than do antibodies against the entirety of human thymidine phosphorylase. As a result, when antibodies against human thymidine phosphorylase fragments are used in the diagnosis of cancers, higher sensitivity can be obtained than in the case where antibodies against the entirety of human thymidine phosphorylase are used. Antibodies obtained using as antigen such human thymidine phosphorylase fragments are immunologically reactive with the entire human thymidine phosphorylase.

It is well known that each of the Fv, Fab, and F(ab')2 fragments of each monoclonal antibody of the present invention has a binding site for the antibody, and that these fragments have ability to bind antigens like complete antibodies. The fragments can be readily obtained via fragmentation of antibodies using a protease.

Diagnostic drugs making use of the monoclonal antibodies of the present invention may be combined with a variety of detection methods in which sensitivity of measurement is attempted to be enhanced, for example, with the avidin-biotin-peroxydase complex (ABC) method in ELISA, the streptoavidin-biotin complex (SBC) method, or the peroxydase-antiperoxydase (PAP) method, etc. The diagnostic drugs may be used singly or in combination with any one of other diagnostic drugs.

The monoclonal antibodies obtained in accordance with the present invention recognize with specificity human thymidine phosphorylase and PD-ECGF, and thus are useful in immunochemical and immunihistological diagnosis of diseases involving promoted thymidine phosphorylase and PD-ECGF activities. Examples of such diseases include, but are not limited to, malignant tumors and metastasis cancers resulting therefrom, rheumatic arthritis, diabetic retinitis, immature cataract, senile macular degeneration, etc. Diagnosis may also be performed using body fluids, because the present antigens are transferred into body fluids as cell death occurs. Diagnostic drugs making use of the monoclonal antibodies of the present invention may be combined with a variety of detection methods in which measurement sensitivity is attempted to be elevated, including the ABC method in ELISA, the SBC method, or with the PAP method. The diagnostic drugs may be used singly or in combination with any one of other diagnostic drugs.

The monoclonal antibodies of the present invention may also be applied to imaging of tissues, e.g., imaging diagnoses using indium-Ign-labelled antibodies.

Moreover, against malignant tumors, the monoclonal antibodies of the present invention can be used in targeting treatment using immunotoxin or the like in which antibody is bound to the active site of lysin or abrin, as reported in Cancer Res., 42, 457–464 (1982).

EXAMPLES

The present invention will next be described by way of examples. However, the present invention is not limited to these examples.

Example 1

Preparation of a binding protein between the N-terminal region or the C-terminal region of an antigen-human thymidine phosphorylase or PD-ECGF and glutathione transferase:

A fusion protein with GST was created using a commercially available kit, GST-gene fusion system (Pharmacia). Briefly, integration into an *E. coli* expression vector was performed so as to obtain a fusion protein between a polypeptide stretching from the 7th residue to the 250th residue in the N-terminal of human thymidine phosphorylase/PD-ECGF and GST, or a fusion protein between a polypeptide stretching from the 353rd residue to the 483rd residue in the C-terminal of human thymidine phosphorylase/PD-ECGF and GST.

The resultant plasmid was introduced into *E. coli* DH 5α, and cultured in 200 ml of an LB medium liquid containing 100 μg/ml of ampicillin until absorbance at the wavelength of 660 nm reached 0.6. When absorbance reached 0.6, isopropyl-β-D(-)-thiogalactopyranoside (IPTG) was added. Culturing was continued for a further 3 hours, after which only *E. coli* cells were collected by centrifugal separation. Collected cells were lysed in an SDS-polyacrylic amide sample buffer, and the solution was subjected to fractional SDS-polyacrylic amide electrophoresis using a device manufactured by Nippon Eido K.K. so as to fractionally obtain a corresponding protein. Yields were 6.4 mg of antigen for the N-terminal side, and 5.7 mg of antigen for the C-terminal side.

Example 2

Cloning of anti-human thymidine phosphorylase or PD-ECGF monoclonal antibody producing cells:

Three 8-week-old female Balb/c mice (supplied by Japan CLER K.K.) were first immunized with a binding protein prepared in Example 1, i.e., a protein prepared by binding the N-terminal region or the C-terminal region of thymidine phosphorylase or PD-ECGF to GST, the binding protein being suspended in complete Freund's adjuvant. Subsequently, a 0.4 ml solution containing 100 μg of a fusion protein was intraperitoneally administered to each mouse. On day 14 from the first immunization, a fusion protein dissolved in a complete Freund's adjuvant was boosted. Further, as a final immunization, auxiliary immunization was intraperitoneally performed on day 10 from the second immunization. Four days thereafter, the spleen of the mouse was removed. The spleen, after gradually homogenized using 3 ml of a growth medium, was subjected to centrifugal separation at 200 G to collect spleen cells.

The collected cells were slowly suspended in an RPMI 1640 medium (PEG 400 solution) containing 50% (V/V) of polyethylene glycol (PEG), and gradually diluted with an RPMI 1640 medium to make the concentration of PEG 5% (V/V). Cells were centrifugally separated. A growth medium was gradually dispersed. Cells were seeded in wells of a microtiter plate in an amount of $10^6$ cells/0.1 ml per well. Cells were incubated in 5% $CO_2$ at 37° C. for 2 minutes.

In this way, mouse spleen cells and myeloma cells P3U1 (P3X 63Ag8U.1) were fused using an electric fusing apparatus.

On the first day after cell fusion, 0.1 ml of an HAT medium was added. Thereafter, a half of the HAT medium was changed to a fresh HAT medium every 3 days. After 8 days, clones emerged. Before the elapse of 10 days, the supernatant was subjected to a solid phase-antibody binding test (ELISA) for screening and checking of the production of IgG.

The positive groups in terms of antibody production were spread in a plate having 24 wells. When the cell density became high, the cells were transferred to a 25 cm² culture. While maintaining hybridomas in an HT medium (an HAT medium without containing aminopterin), antibody production was checked.

In order to obtain clones that react with either the N-terminal or C-terminal of thymidine phosphorylase or PD-ECGF with specificity, screening was performed using an ELISA technique. Briefly, 50 μl of a fusion polypeptide prepared by the use of GST as antigen was added to each well of a 96-well microtiter plate designed for ELISA at a concentration of 10 μg/ml, after which the wells were left overnight at 4° C. Subsequently, 200 μl of a commercially available blocking liquid (product of Dainippon Pharmaceutical Co., Ltd.) was added to each well, and the wells were left at room temperature for 2 hours. A culture supernatant of cloned hybridoma cells was added and incubated at 37° C. for 1 hour.

Peroxidase-labelled anti-mouse IgG antibody (product of Organon Technica) was added so as to achieve a final concentration of 1.0 μg/ml, followed by incubation at 37° C. for 1 hour. Subsequently, 100 μl of an OPDA/aqueous hydrogen peroxide solution was added, and reaction was allowed to proceed for 20 minutes at room temperature. After completion of reaction, reaction was stopped by the addition of 100 μ1 of 2N sulfuric acid. Absorbances at 490 nm and 595 nm were measured using a microtiter reader. Screening was performed based on the difference between the obtained two absorbance data. The results are shown in Tables 1 and 2.

TABLE 1

| | Clones resulted from the N-terminal peptide Absorbance 490–595 nm | | |
|---|---|---|---|
| Clone No. | (1) Immobilized with PD-ECGF/Thymidine Phosphorylase | (2) Immobilized with GST - C-terminal Polypeptide | (1)/(2) × 100 (%) |
| 1D10 | 0.720 | 0.990 | 72.7 |
| 1F4 | 0.700 | 0.875 | 80.0 |
| 2A4 | 0.794 | 0.941 | 84.4 |
| 2A11 | 0.779 | 0.936 | 83.2 |
| 2E6 | 0.747 | 0.929 | 80.4 |
| 3C9 | 0.805 | 0.996 | 80.8 |

Binding assay using respective clones, antigen, and PD-ECGF or thymidine phosphorylase

TABLE 2

| | Clones resulted from the C-terminal peptide Absorbance 490–595 nm | | |
|---|---|---|---|
| Clone No. | (1) Immobilized with PD-ECGF/Thymidine Phosphorylase | (2) Immobilized with GST - C-terminal Polypeptide | (1)/(2) × 100 (%) |
| 1F3 | 0.539 | 0.721 | 74.8 |
| 1F9 | 0.564 | 0.726 | 77.7 |
| 1H10 | 0.595 | 0.812 | 73.3 |
| 2C9 | 0.635 | 0.847 | 75.0 |
| 2D9 | 0.621 | 0.707 | 87.8 |
| 2H8 | 0.642 | 0.734 | 87.5 |

As a result, 6 strains were obtained which were positive for the N-terminal antigen, and 6 strains were obtained which were positive for the C-terminal antigen.

Next, in order to investigate the binding ability of each clone to thymidine phosphorylase/PD-ECGF, screening was performed via ELISA, adding only 1 μg/ml of thymidine phosphorylase/PD-ECGF.

Clones were selected which bound themselves to a fusion protein between GST and the N-terminal thymidine phosphorylase/to PD-ECGF, and which also bound to thymidine phosphorylase/PD-ECGF, so as to obtain clones that bound themselves to both N- or C-terminal peptide and thymidine phosphorylase/PD-ECGF very well (N-terminal clone: 2A4, C-terminal clone: 2D9).

Example 3

Production of anti-thymidine phosphorylase/PD-ECGF monoclonal antibody through cell culturing:

Anti-thymidine phosphorylase antibody-producing hybridomas were subcultured in a 75 cm$^2$-flask for tissue culturing using an RPMI 1640 medium containing 10% (V/V) fetal calf serum,100 mM pyruvic acid, and 2-mercaptoethanol.

When antibody was purified, a serum-free medium, PUF-1 (product of Gibco) was used for culturing.

In this medium, hybridoma cells which propagated to 8×10$^5$ cells/ml were recovered through centrifugal separation at 200 G for 5 minutes.

The collected culture supernatant was concentrated to a volume of not more than 10 ml using a PM 10 ultrafiltration membrane (product of Amicon), followed by filtration through a membrane filter of 0.45 μm.

The thus-obtained crude fraction was combined with an equal amount of a binding buffer, mixed well, and allowed to pass through a protein A column which had been equilibrated using a binding buffer in advance, thereby binding IgG to protein A. The bound product was washed using 10 ml of a binding buffer, after which an IgG fraction was recovered by eluting the IgG in 3 ml of an elution buffer.

To 3 ml of the resultant fraction, 1 ml of 1M Tris HCl buffer (pH 9.0) was added immediately to return the pH in the vicinity of neutrality. Subsequently, dialysis was performed against phosphate-buffered saline (PBS) overnight, thereby obtaining monoclonal antibody IgG with a high purity.

The subclasses of the obtained anti-thymidine phosphorylase antibodies were determined via enzyme immunoassay using a commercially available mouse monoclonal antibody isotyping kit (product of Amersham).

Subclasses of the clones are shown in Tables 3 and 4.

TABLE 3

N-terminal monoclonal antibody-producing clones

| No. of Clones | Subclasses |
| --- | --- |
| 1D10 | IgG1 |
| 1F4 | IgG2a |
| 2A4 | IgG2b |
| 2A11 | IgG2b |
| 2E6 | IgG1 |
| 3C9 | IgG2a |

Immunogloblin subclasses of the clones

TABLE 4

C-terminal monoclonal antibody-producing clones

| No. of Clones | Subclasses |
| --- | --- |
| 1F3 | IgG2a |
| 1F9 | IgG1 |
| 1H10 | IgG2b |
| 2C9 | IgG2b |
| 2D9 | IgG2b |
| 2H8 | IgG3 |

Example 4

Production of anti-thymidine phosphorylase/PD-ECGF monoclonal antibody using mouse ascites:

Hybridoma cells were washed once using a serum-free RPMI 1640 medium, and then resuspended in an RPMI 1640 medium at a concentration of 1×10$^7$ cells/ml.

Hybridoma cells in the number of 5×10$^6$ were intraperitoneally injected to each nude mouse, Balbc/nu-nu, and 2 weeks thereafter, monoclonal antibodies were harvested from the abdominal cavity of the mouse.

The collected ascites was subjected to centrifugal separation at 1500 G for 15 minutes, and then filtered through a membrane filter of 0.45 μm.

The thus-obtained crude fraction was combined with an equal amount of a binding buffer, mixed well, and allowed to pass through a protein A column which had been equilibrated using a binding buffer in advance, thereby binding IgG to protein A. The bound product was washed using 10 ml of a binding buffer, after which an IgG fraction was recovered by eluting the IgG in 3 ml of an elution buffer.

To 3 ml of the resultant fraction, 1 ml of 1M Tris HCl buffer (pH 9.0) was added immediately to return the pH in the vicinity of neutrality. Subsequently, dialysis was performed against phosphate-buffered saline (PBS) overnight, thereby obtaining monoclonal antibody IgG with a high purity.

The subclasses of the obtained anti-thymidine phosphorylase antibodies were determined via enzyme immunoassay using a commercially available mouse monoclonal antibody isotyping kit (product of Amersham).

The subclasses of the clones were identical to those determined in Example 3.

Example 5

Detection of thymidine phosphorylase/PD-ECGF by immunoblotting:

200 μg of a crude protein extract were prepared using cells, normal tissue, or tumor tissue. The extract was analyzed by SDS-polyacrylamide gel electrophoresis using a gradient gel containing 4%–20% (W/V) acrylamide. Subsequently, the protein was electrically transcribed onto a commercially available PVDF membrane (product of Millipore).

After non-specific adsorption was blocked using skim milk, the anti-thymidine phosphorylase/PD-ECGF antibody (clone 2A4) purified in Example 4 was added at a concentration of 0.5 μg/ml. The mixture was allowed to stand at room temperature for 1 hour, and then at 4° C. overnight.

The peroxidase-labelled anti-mouse immunoglobulin used was a commercially available one. Color development of peroxydase was performed using an ECL system (Amersham). The results are shown in FIGS. 1 and 2.

Figure 1B:
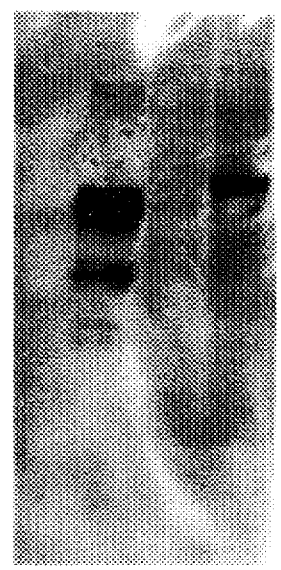

FIG. 1 shows the results of staining of N-terminal antibody 2A4 and C-terminal antibody 2D9, both prepared in Example 4. The fusion protein between GST and the N-terminal polypeptide reacted with 2A4 with specificity, and the fusion protein between GST and the C-terminal polypeptide reacted with 2D9 with specificity. Both antibodies were reactive with over-expressed KB cells obtained by introducing CDNA of thymidine phosphorylase/PD-ECGF, clearly showing a band at the position corresponding to a molecular mass of 55 kD.

FIG. 2 shows the results of comparison between human breast cancerous tissue and its adjacent normal tissue (3 cases). As is understood from the bands at positions corresponding to a molecular mass of 55 kD, higher expression of thymidine phosphorylase/PD-ECGF was observed in each cancerous tissue than in the normal tissue indicated on the right.

The lanes in FIG. 1 are as follows:

GST-N; a polypeptide in which GST was bound to the N-terminal peptide of human thymidine phosphorylase.

GST-C; a polypeptide in which GST was bound to the C-terminal peptide of human thymidine phosphorylase.

KB; a cell extract of KB cells, and

KB-TP; a cell extract of cells obtained by transfecting KB cells with cDNA of human thymidine phosphorylase/PD-ECGF.

Example 6

Immunohistochemical staining of thymidine phosphorylase/PD-ECGF in clinically obtained human tissue slices:

Human malignant tumor tissue and its adjacent normal tissue were excised, and immediately fixed using a 10% (V/V) formalin—PBS. After being left at room temperature for 24 hours, the fixed tissues were embedded in paraffin, and slices each having a thickness of 3 µm were prepared.

After the slices were deparaffinated, a pure thymidine phosphorylase antibody (clone 2A4) purified in Example 4 was added thereto at a concentration of 1 µg/ml, followed by standing at room temperature for 1 hour, and then at 4° C. overnight. The slices were stained using a commercially available kit, Funakoshi ABC ellite kit (product of Vector). The results are shown in FIGS. 3 and 4.

Figure 3:
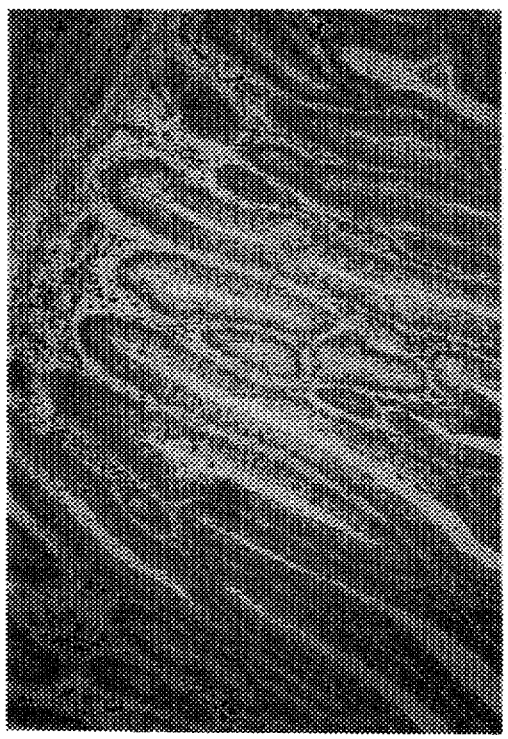
FIG. 3 is a photograph showing the result of immunohistochemical staining of a slice from healthy human large intestine tissue with which a monoclonal antibody of the present invention reacts with specificity.
Figure 4:
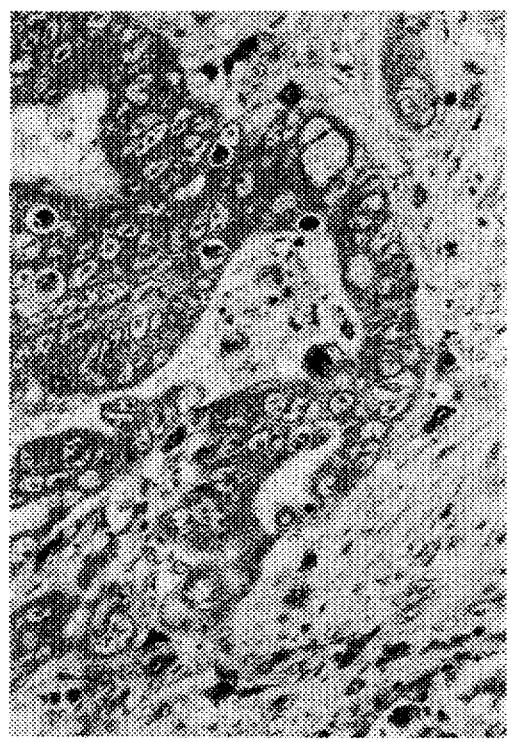
FIG. 4 is a photograph showing the result of immunohistochemical staining of a slice from human large intestinal cancerous tissue with which a monoclonal antibody of the present invention reacts with specificity.

FIG. 3 shows the negative result of staining of a slice from normal tissue. FIG. 4 shows the stained result of large intestinal cancerous tissue. As is clearly understood from these figures, cytoplasm of tumor tissue was positively stained. It was thus found that the antibody is a very useful one, being easy to use and suited in clinical applications, because its reactivity is not lost even after antigenity is degraded due to paraffin fixing, or even after considerable time has elapsed after tissue is excised.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 244 amino acids
      ( B ) TYPE: amino acid
      ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

```
Pro  Gly  Thr  Gly  Ala  Pro  Pro  Ala  Pro  Gly  Asp  Phe  Ser  Gly  Glu  Gly
 1                  5                        10                       15

Ser  Gln  Gly  Leu  Pro  Asp  Pro  Ser  Pro  Glu  Pro  Lys  Gln  Leu  Pro  Glu
                20                       25                       30

Leu  Ile  Arg  Met  Lys  Arg  Asp  Gly  Gly  Arg  Leu  Ser  Glu  Ala  Asp  Ile
                35                       40                       45

Arg  Gly  Phe  Val  Ala  Ala  Val  Val  Asn  Gly  Ser  Ala  Gln  Gly  Ala  Gln
         50                       55                       60

Ile  Gly  Ala  Met  Leu  Met  Ala  Ile  Arg  Leu  Arg  Gly  Met  Asp  Leu  Glu
 65                       70                       75                       80

Glu  Thr  Ser  Val  Leu  Thr  Gln  Ala  Leu  Ala  Gln  Ser  Gly  Gln  Gln  Leu
                     85                       90                       95

Glu  Trp  Pro  Glu  Ala  Trp  Arg  Gln  Gln  Leu  Val  Asp  Lys  His  Ser  Thr
                    100                      105                      110

Gly  Gly  Val  Gly  Asp  Lys  Val  Ser  Leu  Val  Leu  Ala  Pro  Ala  Leu  Ala
               115                      120                      125

Ala  Cys  Gly  Cys  Lys  Val  Pro  Met  Ile  Ser  Gly  Arg  Gly  Leu  Gly  His
     130                      135                      140

Thr  Gly  Gly  Thr  Leu  Asp  Lys  Leu  Glu  Ser  Ile  Pro  Gly  Phe  Asn  Val
145                      150                      155                      160

Ile  Gln  Ser  Pro  Glu  Gln  Met  Gln  Val  Leu  Leu  Asp  Gln  Ala  Gly  Cys
                    165                      170                      175
```

```
Cys  Ile  Val  Gly  Gln  Ser  Glu  Gln  Leu  Val  Pro  Ala  Asp  Gly  Ile  Leu
          180                           185                      190

Thr  Ala  Ala  Arg  Asp  Val  Thr  Ala  Thr  Val  Asp  Ser  Leu  Pro  Leu  Ile
          195                      200                     205

Thr  Ala  Ser  Ile  Leu  Ser  Lys  Lys  Leu  Val  Glu  Gly  Leu  Ser  Ala  Leu
          210                 215                      220

Val  Val  Asp  Val  Lys  Phe  Gly  Gly  Ala  Ala  Val  Phe  Pro  Asn  Gln  Glu
225                           230                 235                          240

Gln  Ala  Arg  Glu
```

( 2 ) INFORMATION FOR SEQ ID NO:2:

( i ) SEQUENCE CHARACTERISTICS:
        ( A ) LENGTH: 130 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:2:

```
Asp  Pro  Gly  Leu  Ala  Arg  Ala  Leu  Cys  Ser  Gly  Ser  Pro  Ala  Glu  Arg
1                   5                        10                      15

Arg  Gln  Leu  Leu  Pro  Arg  Ala  Arg  Glu  Gln  Glu  Glu  Leu  Leu  Ala  Pro
               20                       25                      30

Ala  Asp  Gly  Thr  Val  Glu  Leu  Val  Arg  Ala  Leu  Pro  Leu  Ala  Leu  Val
          35                      40                      45

Leu  His  Glu  Leu  Gly  Ala  Gly  Arg  Ser  Arg  Ala  Gly  Glu  Pro  Leu  Arg
     50                      55                      60

Leu  Gly  Val  Gly  Ala  Glu  Leu  Leu  Val  Asp  Val  Gly  Gln  Arg  Leu  Arg
65                       70                 75                            80

Arg  Gly  Thr  Pro  Trp  Leu  Arg  Val  His  Arg  Asp  Gly  Pro  Ala  Leu  Ser
               85                      90                      95

Gly  Pro  Gln  Ser  Arg  Ala  Leu  Gln  Glu  Ala  Leu  Val  Leu  Ser  Asp  Arg
               100                     105                     110

Ala  Pro  Phe  Ala  Ala  Pro  Ser  Pro  Phe  Ala  Glu  Leu  Val  Leu  Pro  Pro
          115                      120                     125

Gln  Gln
130
```

Hybridomas 2A4 and 2D9 described in the present application were deposited at the National Institute of Bioscience and Human-Technology Agency of Industrial Science and Technology, 1–3, Higashi 1 chome Tsukuba-shi, Ibaraki-ken 305, JAPAN, on Oct. 14, 1997, under FERM BP-6142 and FERM BP-6143, respectively.

Industrial Utility

Since the monoclonal antibodies of the present invention enable measurement of thymidine phosphorylase/PD-ECGF with specificity and provide a practical means which is simple and widely applicable, the monoclonal antibodies are useful for the diagnosis of a variety of diseases accompanying elevation in human thymidine phosphorylase or PD-ECGF activity.

We claim:

1. A monoclonal antibody having binding specificity to a peptide having the amino acid sequence of SEQ ID NO:1, or an epitope thereof, wherein said monoclonal antibody is 2A4 produced by hybridoma FERM BP-6142, and is of the $IgG_{2b}$ subclass.

2. A monoclonal antibody having binding specificity to a peptide having the amino acid sequence of SEQ ID NO:2, or an epitope thereof, wherein said monoclonal antibody is 2D9 produced by hybridoma FERM BP-6143, and is of the $IgG_{2b}$ subclass.

3. An immunoassay for detecting human thymidine phosphorylase/human platelet-derived endothelial cell growth factor comprising the steps of:

(A) reacting a body fluid or tissue sample with a monoclonal antibody having binding specificity to a peptide having the amino acid sequence of SEQ ID NO:1, or an epitope thereof, wherein said monoclonal antibody is 2A4 produced by hybridoma FERM BP-6142, and is of the $IcG_{2b}$ subclass; and (B) determining whether said monoclonal antibody binds to proteins in said body fluid or tissue sample.

4. The immunoassay as claimed in claim 3, wherein said immunoassay is an immunohistochemical staining assay.

5. An immunoassay for detecting human thymidine phosphorylase/human platelet-derived endothelial cell growth factor comprising the steps of:

(A) reacting a body fluid or tissue sample with a monoclonal antibody having binding specificity to a peptide having the amino acid sequence of SEQ ID NO:2, or an epitope thereof, wherein said monoclonal antibody is 2D9 produced by hybridoma FERM BP-6143, and is of the $IaG_{2b}$ subclass; and (B) determining whether said monoclonal antibody binds to proteins in said body fluid or tissue sample.

6. The immunoassay as claimed in claim 5, wherein said immunoassay is an immunohistochemical staining assay.

* * * * *